United States Patent [19]

Tsien et al.

[11] Patent Number: 5,374,710
[45] Date of Patent: Dec. 20, 1994

[54] COMPOUNDS WHICH RELEASE NITRIC OXIDE UPON ILLUMINATION

[75] Inventors: Roger Y. Tsien, LaJolla; Lewis R. Makings, San Diego, both of Calif.

[73] Assignee: Regents of the University of California, Oakland, Calif.

[21] Appl. No.: 67,657

[22] Filed: May 26, 1993

[51] Int. Cl.⁵ .................. C07C 245/02; C07C 245/24; C01B 21/24
[52] U.S. Cl. ................................ 534/552; 534/556; 534/569; 423/405
[58] Field of Search ............... 534/552, 556, 569; 514/151

[56] References Cited

U.S. PATENT DOCUMENTS

| | | | |
|---|---|---|---|
| 3,714,351 | 1/1973 | Gubler | 514/151 |
| 3,907,767 | 9/1975 | Hess et al. | 534/552 |
| 3,962,434 | 6/1976 | Miesel | 514/151 |
| 4,297,096 | 10/1981 | Yoshida et al. | 534/552 |
| 5,155,137 | 10/1992 | Keefer et al. | |

FOREIGN PATENT DOCUMENTS

| | | | |
|---|---|---|---|
| 62-273941 | 11/1987 | Japan | 534/552 |
| 1747438 | 7/1992 | U.S.S.R. | 534/552 |

OTHER PUBLICATIONS

Behera et al, Spectrochimica Acta, vol. 27A, pp. 2273 to 2275 (1971).
Adams, et al., "Controlling Cell Chemistry with Caged Compounds", *Annu. Rev. Physiol.* 55:755–84 (1993).
Bliss, et al., "A Synaptic Model of Memory: Long-Term Potentiation in the Hippocampus", *Nature* 361:31–39 (7 Jan. 1993).
Bohn et al., "Oxygen and Oxidation Promote the Release of Nitric Oxide from Sydnonimines", *J. Cardiovascular Pharm.* 14(Suppl. II):S6–S12 (1989).
Boulton et al., "Nitric Oxide Induces Transient Synaptic Depression in Rat Hippocampal Slices", *J. Physiol. Abstract C37* p. 51P (Leeds Meeting 1993).
Carter et al., "Photochemical Release of Nitric Oxide form Ruthenium Nitrosyl Trichloride: Relaxation of Rabbit Isolated Aortic Rings Mediated by Photo-release of Nitric Oxide", *J. Physiol. Abstract C20* p. 34P (Leeds Meeting 1993).
Drago et al., "The Reaction of Nitrogen (II) Oxide with Various Primary and Secondary Amines", *J. Am. Chem. Soc.* 83:1819–1822 (1961).
Drago et al., "The Reaction of Nitrogen (II) Oxide with Diethylamine", *J. Am. Chem. Soc.* 82:90–98 (1960).
Flitney et al., "Photochemical Release of Nitric Oxide from Iron–Sulphur Cluster Nitrosyls: Laser Potentiation of Vasodilator Actions on Rat Isolated Tail Artery", *J. Physiol.* 459:90P (1993).
Flitney et al., "Selective Retention of Iron–Sulphur Cluster Nitrosyls in Endothelial Cells of Rat Isolated Tail Artery: Association with Protracted Vasodilator Responses", *J. of Physiol.* 459:89P (1993).
Hallam et al., "Agonists Stimulate Divalent Cation Channels in the Plasma Membrane of Human Platelets", *FEBS Lett.* 186175–179 (1985).

(List continued on next page.)

*Primary Examiner*—Floyd D. Higel
*Attorney, Agent, or Firm*—Robbins, Berliner & Carson

[57] ABSTRACT

Chemical derivatives of nitric oxide are provided which are stable indefinitely in oxygen-containing solutions until photolysis, whereupon they release NO. These compounds have the general formula $$A-N^+(O^-)=N-O-B \qquad (I)$$

wherein A is typically a nitrogen- or oxygen-containing substituent and B is a group labile to photolysis. The compounds are stable and inert in oxygenated aqueous solutions, but release NO upon illumination. Given the ease with which the intensity, timing and location of illumination may be controlled, these compounds are particularly useful in investigating the biological effects of NO with much higher spatial or temporal resolution than heretofore possible.

5 Claims, 4 Drawing Sheets

OTHER PUBLICATIONS

Hrabie et al., "New Nitric Oxide-Releasing Zwitterions Derived from Polyamines", *J. Org. Chem.* 58:1472–1476 (1993).

Maragos et al., "Complexes of NO with Nucleophiles as Agents for the Controlled Biological Release of Nitric Oxide", *J. Med. Chem.* 34:3242–3247 (1991).

McCray et al., "Properties and Uses of Photoreactive Caged Compounds", *Annu. Rev. Biophys. Chem.* 18:239–70 (1989).

Moncada et al., "Nitric Oxide: Physiology, Pathophysiology, and Pharmacology", *Pharmacolog. Review* 43:109–142 (1991).

Saavedra et al., "Secondary Amine/Nitric Oxide Complex Ions, $R_2N[N(O)NO]$ O-Functionalizaiton Chemistry", *J. Org. Chem.* 57:6134–6138 (1992).

Williams et al., "Photolytic Release of Nitric Oxide from Ruthenium Nitrosyl Chloride Depresses an APS-Sensitive Response But Does Not Induce Long-Term Potentiation in Area CA1 of the Rat Hippocampus In Vitro", *J. Physiol. Abstract C19* p. 33P (Leeds Meeting 1993).

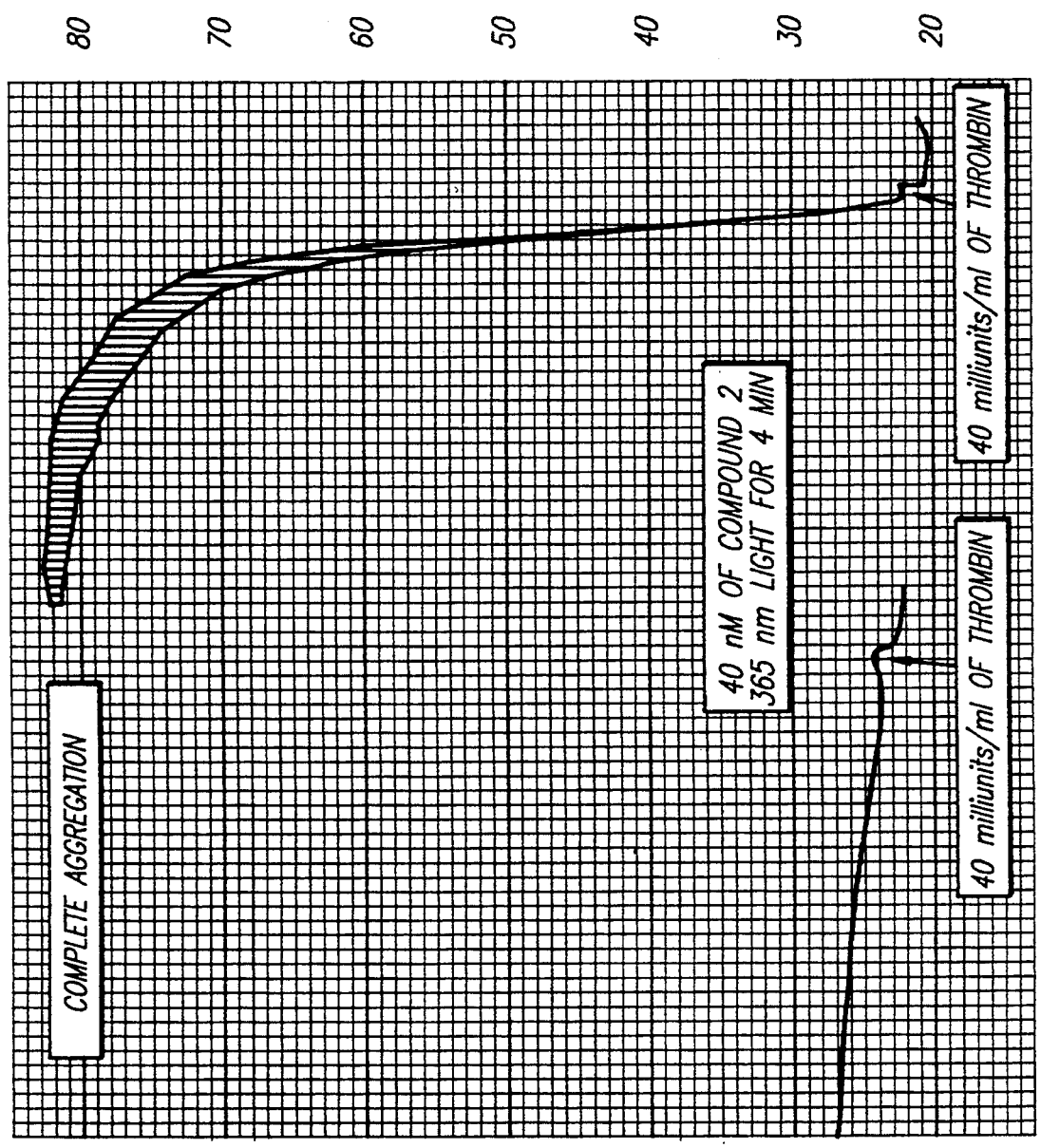

COMPOUNDS WHICH RELEASE NITRIC OXIDE UPON ILLUMINATION

BACKGROUND OF THE INVENTION

The present invention relates to generally to the fields of organic chemistry and biochemistry. In particular, the present invention is directed to compounds which release nitric oxide (NO) in a controlled manner, as well as methods for the preparation and use thereof.

Nitric oxide has been implicated in a variety of important bioregulatory processes [for a review, see Moncada, S. et al., "Nitric Oxide: Physiology, Pathophysiology, and Pharmacology," *Pharmacolog. Rev.* 43:109–142 (1991). For example, nitric oxide has been identified as the endogenous stimulator of the soluble guanylate cyclase; in this role, NO can be considered the endogenous nitrovasodilator and NO-dependent vasodilator tone is probably one of the most fundamental adaptive mechanisms in the cardiovascular system. In addition, NO is an effector molecule released by murine macrophages and other cells after immunological activation.

NO is synthesized from the amino acid L-arginine by an enzyme, NO synthase; the precise mechanism for the biosynthesis has not, however, been eludicated. It is believed that there are at least two forms of the enzyme: a constitutive form which releases NO for short periods in response to receptor or physical stimulation; and a second form which is induced after activation of macrophages, endothelial cells and certain other cells by cytokines and which, once expressed, synthesizes NO for extended periods.

The constitutive form of NO synthase is implicated in the transduction mechanism for soluble guanylate cyclase, and thus in one of the mechanisms whereby cells regulate their own function or communicate with others. In addition, the release of NO in the cardiovascular system acts as a general adaptive mechanism whereby the vascular endothelium responds to changes in its environment and regulates blood flow and blood pressure through an action on the vascular smooth muscle. NO also regulates the interaction between the endothelium and the platelets (and probably blood-borne cells); it may also play a role in the control of vascular smooth muscle proliferation. The NO released by the constitutive enzyme may also play regulatory roles in other cells; for example, it is known to be linked to the stimulation by the excitatory antino acids of specific receptors in the central nervous system, and it may participate in the regulation of the secretion or action of various hormones.

NO released after immunological stimulation by the other form of the enzyme as part of the host defense mechanism has been shown to be cytotoxic or cytostatic for tumor cells and invasive organisms. Further, some forms of local or systemic tissue damage associated with immunological conditions could prove to be related as well to the release of NO. NO may also play a role in the normal regulation of the response of cells to mitogens, or contribute to the cytotoxic actions of other cells that play a role in specific immunity.

An elucidation of the biological roles of NO is complicated by the fact that most of the details about the function, distribution, and interaction of the two forms of enzyme involved in the synthesis of NO have yet to be studied. NO is itself extremely poisonous and unstable in the presence of oxygen. It is a highly reactive gas in its pure form, attacking most metals and plastics, and can only be obtained in relatively low pressure cylinders. Moreover, NO has limited solubility in aqueous media, making it difficult to introduce reliably into most biological systems without premature decomposition. In view of the central importance of NO as both a transducer and as an effector molecule, however, it is apparent that agents for the controlled release of NO would be invaluable in the continued research on the roles of NO in human physiology and pathology. Moreover, the therapeutic potential of agents which may be employed to release NO in a controlled manner is enormous.

Various vasodilators are known which release NO either spontaneously or upon activation by chemical or enzymatic means. For example, the release of NO from molsidomine (N-ethoxycarbonyl-3-morpholinosydnonimine) begins with an enzymatic hydrolysis catalyzed mainly by liver esterases, followed by a pH-dependent ring opening reaction catalyzed by hydroxyl ions; a subsequent oxidative process is then essential for further decomposition and NO release [Bohn, H. and K. Schoenafinger, "Oxygen and Oxidation Promote the Release of Nitric Oxide from Sydnonimines," *J. Cardiovasc. Pharmacol.* 14(Suppl.11):S6–S12 (1989)]. The vasodilators glyceryl trinitrate and sodium nitroprusside release nitric oxide upon redox activation. Other agents, such as iron-sulfur cluster nitrosyls, decompose spontaneously to release NO [Flitney, F.W. et al., "Selective retention of iron-sulphur cluster nitrosyls in endothelial cells of rat isolated tail artery: association with protracted vasodilator responses, *J. Physiol.* 459:89P (1993)].

Agents of the structure XN(O-)N=O, where X is a nucleophile residue, have been proposed as vehicles for the controlled delivery of NO into a biological system [Maragos, C. M. et al., "Complexes of NO with Nucleophiles as Agents for the Controlled Biological Release of Nitric Oxide. Vasorelaxant Effects," *J. Medicinal Chem.* 34:3242–3247 (1991)]. By varying the structure of the nucleophile residue, compounds having a range of decomposition rates and extents of nitric oxide release were prepared; the half-lives at 37° C. and pH 7.4 ranged from 2.1 to 39 minutes. In addition, the vasoactivity of these compounds was correlated with the quantity of NO generated under the test conditions. A series of compounds (in which X=Et$_2$N) prepared by reaction of the ion with a variety of electrophiles exhibited even greater stability; the products of these alkylations were found to be remarkably resistant to hydrolysis [Saavedra, J. E. et al., "Secondary Amine/Nitric Oxide Complex Ions, R$_2$N[N(O)NO]-. O-Functionalization Chemistry," *J. Org. Chem.* 57:6134–6138 (1992)]. A similar range of half-lives in solution were observed with zwitterionic polyamine/NO adducts prepared by reaction of NO with polyamines; the products were stable in solid form [Hrabie, J. A. et at., "New Nitric Oxide-Releasing Zwitterions Derived From Polyamines," *J. Org. Chem.* 58:1472–1476 (1993); U.S. Pat. No. 5,155,137 to Keefer et al., the entire disclosure of which is hereby incorporated by reference]. While some of these compounds may have potential utility as prodrugs, they nonetheless either decompose spontaneously or are dependent upon chemical and/or enzymatic activation for release of NO. Thus, these compounds are essentially simple variants of the heretofore-known vasodilator compositions.

For a variety of experimental uses, it would be particularly advantageous if the release of NO from an agent could be substantially prevented until the agent is activated by the researcher, for example by illumination. It has been reported that release of nitric oxide from an iron-sulfur cluster nitrosyl (Roussin's 1858 "black" salt, or RBS) is accelerated by exposure to laser light [Boulton, C. L. et al., "Nitric Oxide induces transient synaptic depression in rat hippocampal slices," *J. Physiol,* Abstract C37, p. 51P (Leeds Meeting 1993); Flitney, F. W. et al., "Photochemical release of nitric oxide from iron-sulphur cluster nitrosyls: laser potentiation of vasodilator actions on rat isolated tail artery," *J. Physiol.* 459:90P (1993)]. Ruthenium nitrosyl chloride salts have also been used as agents for delivery of NO upon exposure to near-UV irradiation [Williams, J. H. et al., "Photolytic release of nitric oxide from ruthenium nitrosyl chloride depresses an APS-sensitive response but does not induce long-term potentiation in area CA1 of the rat hippocampus in vitro," *J. Physiol.,* Abstract C19, p. 33P (Leeds Meeting 1993); Carter, T. D. et al., "Photochemical release of nitric oxide from ruthenium nitrosyl trichloride: relaxation of rabbit isolated aortic rings mediated by photorelease of nitric oxide," *J. Physiol.,* Abstract C20, p. 34P (Leeds Meeting 1993). Unfortunately, these agents comprise metals which themselves may interfere with the physiological phenomena under investigation or may be toxic. Therefore, there remains a need for additional agents useful for the delivery of NO which do not suffer from the drawbacks of the heretofore-known compositions. Such compositions would be very useful in a number of fields, such as biochemistry, cell biology and neurobiology.

It is an object of the present invention to provide compositions for delivery of nitric oxide which remain stable until it is desired to release NO by a particular triggering means, as well as methods for the preparation and use thereof.

SUMMARY OF THE INVENTION

Pursuant to the present invention, there are provided chemical derivatives of nitric oxide which are stable indefinitely in oxygen-containing solutions until photolysis, whereupon they release NO. These compounds have the general formula

$$A-N^+(O^-)=N-O-B \qquad (I)$$

wherein A is a substituent as hereinafter defined and B is a group labile to photolysis. The compounds are stable and inert in oxygenated aqueous solutions, but release NO upon illumination. Given the ease with which the intensity, timing and location of illumination may be controlled, these compounds are particularly useful in investigating the biological effects of NO with much higher spatial or temporal resolution than heretofore possible.

BRIEF DESCRIPTION OF THE DRAWINGS

The invention may be better understood with reference to the accompanying drawings, in which

FIG. 4 illustrates the results of a typical platelet aggregation experiment.

DETAILED DESCRIPTION OF THE INVENTION

Figure 1:
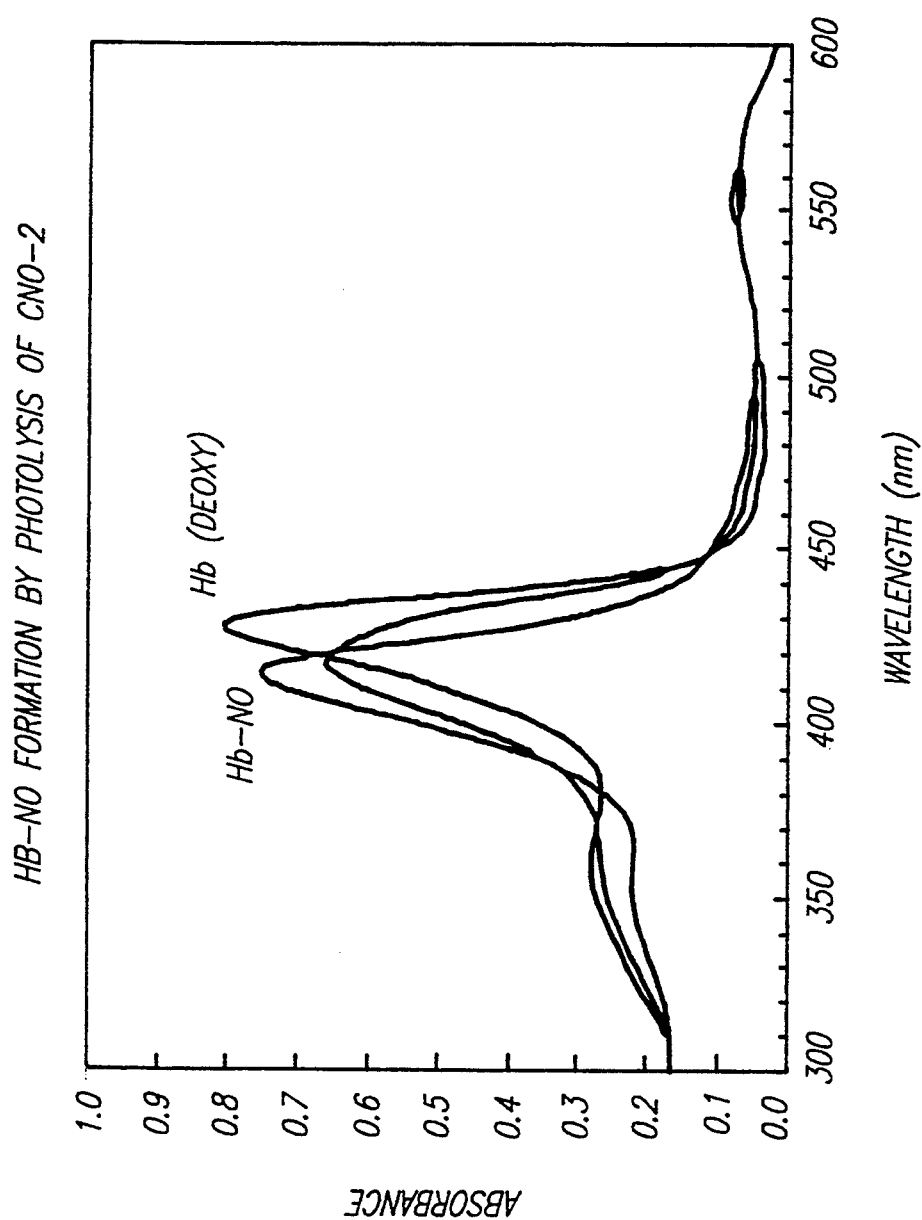
FIG. 1 shows the conversion of a 7 μM (heme basis) solution of Hb in 50 mM phosphate to Hb-NO.

Pursuant to one aspect of the present invention, there are provided compounds of the general formula I

$$A-N^+(O^-)=N-O-B \qquad (I)$$

wherein A is selected from the group consisting of $-NR^1R^2$, 1- imidazolyl and $-OR^3$, in which $R^1$ is selected from the group consisting of hydrogen and $C_1-C_{12}$ alkyl, $R^2$ is selected from the group consisting of hydrogen, $C_1-C_{12}$ alkyl, $-(CR''_2)y\, NR'_2$, $-CR''_2CO_2R'$, $-CR''_2CO_2CR''_2O_2CR''$ and $-C(CO_2R'')R''R^4$, $R^3$ is selected from the group consisting of hydrogen, $C_1-C_{12}$ alkyl, $-C_6H_5$ and B (as hereinafter defined), each $R'$ is independently selected from the group consisting of hydrogen, lower alkyl, $-(CR''_2)yNR''_2$, $-CR''_2CO_2R''$ and $-CR''_2CO_2CR''_2O_2CR''$, $R''$ is hydrogen or lower alkyl, each y is an integer from 1 to 6 and $R^4$ is an amino acid sidechain residue; and B is a group labile to photolysis. For purposes of the present invention, a group labile to photolysis is one which dissociates from the balance of the $A-N^+(O^-)-=N-O-B$ molecule upon irradiation of the molecule with light at a particular wavelength in the UV and/or visible spectrum; upon irradiation to release the labile group B, NO is also simultaneously released from the previously stable structure. A wide variety of groups labile to photolysis, referred to as "caging" structures, are known in the art; for example, the properties of various 2-nitrobenzyl derivatives are discussed in McCray, J. A. and Trentham, D. R., "Properties and Uses of Photoreactive Caged Compounds," *Annu. Rev. Biophys. Chem.* 18:239–70 (1989) and Adams, S.R. and Tsien, R. Y., "Controlling Cell Chemistry with Caged Compounds," *Annu. Rev. Physiology* 55:755-784 (1992), the entire disclosures of which are hereby incorporated by reference. Among the structures suitable for use as group B in compounds in accordance with the present invention are the following: 2-nitrobenzyl and various α-substituted derivatives thereof, such as 2-(2nitrophenyl)ethyl and α-carboxy-2-nitrobenzyl, which dissociate at a wavelength of about 265 nm; 2,2'-dinitrobenzhydryl, which also dissociates at a wavelength of 265 nm; 4,5-dimethoxy-2-nitrobenzyl, 1-(4,5-dimethoxynitrophenyl)ethyl and bis(2-nitro-4,5-dimethoxyphenyl)-methyl, all of which dissociates at 385 nm; α-benzoyl-3,5-dimethoxybenzyl, which dissociates at 246 nm; 3,5-dinitrophenyl, which dissociates in the presence of water at 340 nm; and (4-methoxy-8 azido-1naphthyl)-methyl, which dissociates at 319 nm.

For purposes of the present invention, by lower alkyl is meant alkyl groups of 1–5 carbon atoms. Both $C_1-C_{12}$ alkyl and lower alkyl include straight-chain and branched groups, as well as cycloalkyl. By an amino acid side-chain residue is meant a substituent characteristic of the naturally-occurring amino acids; these include, for example, alkyl (as in alanine, valine and leucine), hydroxyalkyl (as in serine and threonine) and aralkyl residues (as in phenylalanine, histidine and tryptophan). Any of the groups in general formula I may in addition bear one or more non-interfering substituents. By non-interfering substituents is meant substituents which do not engage in undesirable side-reactions and which do not hinder photolysis due to steric and/or electronic factors. For example, suitable non-interfering substituents include alkyl, phenyl, alkoxy, phenoxy, carboxyl, alkylcarbonyl, alkoxycarbonyl, alkylamino and aminoallcyl (which may be protected in a manner known per se, for example as described in the aforementioned U.S. Pat. No. 5,155,137), halogen, and protected hydroxy (i.e., a hydroxyl group which is protected by one of a variety of protective groups which are known per se) and the like.

A preferred class of groups B have the general formula

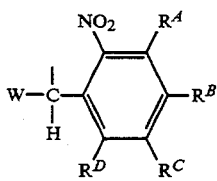

wherein $R^A$ is selected from the group consisting of hydrogen, lower alkyl, lower alkoxy, —$(CR''_2)_ySR'$, —$(CR''_2)_yNR''_2$, —$CO_2R$ and —$OCR''_2CO_2R$, in which R is selected from the group consisting of hydrogen, $C_1$–$C_{12}$ alkyl and —$(CR''_2)_yO_2CR'$, and R', R'' and y are as previously defined;

each of $R^B$ and $R^C$ is independently selected from the group consisting of hydrogen, lower alkyl, lower alkoxy, —$CO_2R$ and —$OCR''_2CO_2R$, or $R^B$ and $R^C$ taken together are —$O(CR''_2)_xO$—, in which x is 1 or 2;

$R^D$ is selected from the group consisting of $NO_2$, hydrogen, lower alkyl, lower alkoxy, —$(CR''_2)_ySR'$, —$CO_2R$, —COR and —$OCR''_2CO_2R$; and W is selected from the group consisting of hydrogen, lower alkyl, $CO_2R''$ and

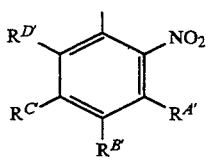

wherein each of $R^{A'}$, $R^{B'}$, $R^{C'}$ and $R^{D'}$ is independently defined in the same manner as $R^A$, $R^B$, $R^C$ and $R^D$, respectively.

One particularly preferred class of groups B are those wherein $R^A$ and $R^D$ are hydrogen, $R^B$ and $R^C$ are hydrogen or lower alkoxy and W is hydrogen, lower alkyl or

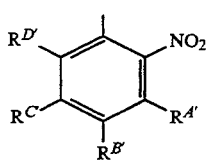

wherein each of $R^{A'}$, $R^{B'}$, $R^{C'}$ and $R^{D'}$ is independently defined in the same manner as $R^A$, $R^B$, $R^C$ and $R^D$, respectively. These structures labile to photolysis have been studied intensively and methods for the preparation thereof are well known in the art.

Another particularly preferred class of groups B are those in which $R^A$ and $R^D$ are hydrogen, $R^B$ and $R^C$ are —$CO_2R$ or —$OCR''_2CO_2R$, in which R is selected from the group consisting of hydrogen and —$(CR''_2)O_2CR'$ in which R' is hydrogen or lower alkyl, and W is hydrogen, lower alkyl or

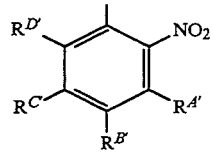

wherein each of $R^{A'}$, $R^{B'}$, $R^{C'}$ and $R^{D'}$ is independently defined in the same manner as $R^A$, $R^B$, $R^C$ and $R^D$, respectively. Compounds containing a group B of this class are relatively impermeant through membranes due to the added negative charges produced either by ionization or hydrolysis and would thereby permit trapping of the NO releaser in defined cellular compartments before photolysis, thus mimicking cell-specific generation of NO.

All of the compounds of general formula I are stable and inert in aqueous solutions, even when the solutions are oxygenated. Upon illumination, however, the group labile to photolysis dissociates from the balance of the molecule and NO is released. The rate of photorelease of NO for several of the compounds was measured by using absorption spectrophotometry of deoxyhemoglobin or microperoxidase and appears to be surprisingly rapid (half-life of <5 milliseconds). Moreover, unlike many of the heretofore-known structures, release of NO is not dependent upon poorly-understood redox activation and/or enzyme metabolism; the timing of NO release may be precisely controlled by controlling the illumination.

A further advantage of the compounds of the present invention relative to prior art carriers of NO is that the inventive compounds do not produce superoxide in addition to NO. For example, manganese-substituted hemoglobin (which releases NO upon photoactivation) and syndonimine derivatives (which release NO upon redox activation) form superoxide in the course of releasing nitric oxide. The combination of nitric oxide and superoxide is known to be more toxic than nitric oxide alone. Thus, for most purposes it is highly advantageous to employ the compounds of the present invention in lieu of the heretofore-known alternatives.

The compounds of the present invention may be prepared by a variety of synthetic routes. Most generally, one particularly useful route involves the reaction of a compound of general formula II $$A—N^+(O^-)=N—O—Na \qquad (II)$$

with a compound of general formula III $$B—X$$

in which X is a suitable leaving group (for example, halogen, tosylate, brosylate, etc.). This reaction is suitably carried out at room temperature and under an inert atmosphere (such as argon). The compounds of formula II may be prepared, for example, by a method as described in Drago, R. S. and Paulik, F. E., *J. Am. Chem. Soc.* 82:90–98 (1960) and Drago, R. S. and Karstetter, B. R., *J. Am. Chem. Soc.* 83:1819–1822 (1961), the entire disclosures of which are hereby incorporated by reference. The compounds of general formula III are either readily available or may be prepared from available compounds in a manner known per se.

The compounds are particularly useful as means for delivering NO both in vitro and in vivo for investigative and therapeutic purposes. In a number of experiments such as the study of long term potentiation (LTP) or long term depression (LTD) in brain slices, for example, introduction of a compound in accordance with the present invention into a single cell can be accomplished by injection with a micropipette. Once inside, the nitric oxide donor would be expected to remain in the cell; this is particularly true with those compounds of the invention, such as 1-[(4', 5'-bis(carboxylmethyloxy)-2'-nitrophenyl)methyloxo]-2-oxo-3,3-diethyl 1triazene potassium salt, that are designed to be membrane impermeable. This technique is extremely valuable in the highly active field of study of the effects of NO, as indiscriminate application of nitric oxide has heretofore produced a number of contradictory results [Bliss, T. V. P. and G. L. Coilingridge, Nature 361:31–39 ( 1993)].

The results of platelet experiments further demonstrate the very desirable properties of these nitric oxide donors. For example, a compound of the invention such as 1-[(4', 5 '-bis(carboxymethoxy)-2'-nitrophenyl)methoxy]-2-oxo-3,3-diethyl-1-triazene acetoxymethyl ester may be loaded into all cells of a preparation by addition thereof to the cell buffer. Nitric oxide can then be easily titrated to an appropriate concentration for the particular experiment to be performed. In addition, using a highly focused light source (e.g., through the optics of a microscope) small areas of cells or even single cells can be stimulated with nitric oxide. The loading of a nitric oxide donor in accordance with the invention into a large population of suspended cells, washing and then mixing of the loaded cells with a different population or type of cells or bacteria may be used to mimic the pathophysiological properties of nitric oxide and its involvement in the immune system. These types of experiments could only be accomplished with the nitric oxide donor compounds of the present invention.

The invention may be better understood with reference to the accompanying examples, which are intended for purposes of illustration only and should not be construed as in any sense limiting the scope of the invention as defined in the claims appended hereto.

EXAMPLES

Chemicals and solvents (HPLC-grade) were used directly as obtained unless otherwise noted. Dimethylformamide (DMF), diisopropylethylamine (DIEA), methylene chloride, methanol, and toluene were dried over 3 Angstrom molecular sieves.

Proton magnetic resonance spectra ($^1$NMR) were recorded on a Varian Gemini 200-MHZ spectrometer in CDCL$_3$ unless otherwise noted; the chemical shifts are given in δ values relative to tetramethylsilane. Ultraviolet-Visible (UV-VS) absorbance spectra were recorded on a Perkin-Elmer Lambda Array 3840 spectrophotometer at ambient temperature.

EXAMPLE 1

Preparation of 1-[(2'-nitrophenyl)methoxy]-2-oxo-3,3-diethyl-1-triazene

To an argon purged solution of 100 ml of diethylamine in 200 ml of ether, nitric oxide was introduced at atmospheric pressure while maintaining the solution at −78° C. After 16 hours, the solution was purged with argon and warmed to 5° C. The solution was quickly filtered and evaporated to give 6.05 g of a slightly yellow solid. To 2.8 g (13.6 mmol) of this diethyl ammonium salt dissolved in 5 ml of ethanol was added 13 ml of 1 M sodium ethoxide. After 15 minutes, 200 ml of ether is added and the solution is cooled at −20° C. for 24 hours. The chilled solution is quickly filtered and the precipiate washed with chloroform under argon. After drying under vacuum, 1.59 g of 1-hydroxy-2-oxo-3,3-diethyl-1-triazene sodium salt [Et$_2$N(N$_2$O$_2$)Na] was obtained as a white powder.

Et$_2$N(N$_2$O$_2$)Na (100 mg, 0.65 mmol) and 2-nitrobenzyl bromide (120 mg, 0.56 mmol) were dissolved in 1 ml of dry DMF. The mixture was stirred for 30 minutes under an argon atmosphere at room temperature. The reaction mixture was diluted with toluene (5 ml) and extracted with water (3×3 ml). After drying over sodium sulfate, the solvent was evaporated to yield crude product which was further purified by silica gel chromatography eluting with ethyl acetate/hexane (1:3) to give 72 mg (48% yield) of a colorless oil 1. $^1$NMR: δ 1.06 (t, 6H, NCH$_2$CH$_3$, 3.13 (q, 4H, NCH$_2$CH$_3$), 5.72 (s, 2H, OCH$_2$Ar), 7.48 (m 1H, ArH), 7.64 (m, 2H, ArH), 8.15 (d, 1H, ArH).

EXAMPLE 2

Preparation of 1-[(4', 4'-dimethoxy-2'-nitrophenyl)methoxy]-2-oxo-3,3-diethyl-1triazene To a solution of Et$_2$N(N$_2$O$_2$)Na (195 mg, 1.25 mmol) prepared as in Example 1 in 3 ml of dry DMF was added 1-(bromomethyl)-4,5,-dimethoxy-2-nitrobenzene (275 mg, 1.0 mmol; prepared as described in Wilcox et al., J. Org. Chem. 55:1585 (1990). The reaction mixture was stirred under an argon atmosphere for 2 hr at room temperature. The reaction mixture was diluted with toluene (30 ml) and extracted with water (3×5 ml). The toluene over was dried sodium sulfate, filtered and evaporated to yield 290 mg of crude product as an oil. The product was further purified by silica gel chromatography, eluting with ethyl acetate/hexane (1:3). The resulting yellow solid was triturated with ethyl acetate/hexane (1:10) to give 112 mg (34% yield) of a white solid 2. $^1$NMR: δ 1.08 (t, 6H, NCH$_2$CH$_3$), 3.16 (q, 4H, NCH$_2$CH$_3$), 3.95 (s, 3H, OCH$_3$), 3.96 (s, 3H, OCH$_3$), 5.73 (s, 2H, OCH$_2$Ar), 7.11 (s, 1H, ArH), 7.74 (s, 1H, ArH).

EXAMPLE 3

Preparation of 1-[(4',4'-dimethoxy-2'-nitrophenyl)ethoxy]-2-oxo-3,3-diethyl- 1triazene To a solution of Et$_2$N(N$_2$O$_2$)Na (70 mg, 0.45 mmol) prepared as in Example 1 in 1 ml of dry DMF was added 1-(α-bromoethyl)-4,5,-dimethoxy-2-nitrobenzene (110 mg, 0.38 mmol; prepared using the method described in Wilcox et al, supra). The reaction mixture was stirred under an argon atmosphere for 2 hr at room temperature. The reaction mixture was then diluted with toluene (10 ml) and extracted with water (3×5 ml). The toluene was dried over sodium sulfate, filtered and evaporated to give the crude product as an oil. The product was further purified by silica gel chromatography eluting with ethyl acetate/hexane (1:3). The resulting yellow solid was triturated with ethyl acetate/hexane (1:5) to give 52 mg (40% yield) of a white solid 3. $^1$NMR: δ0.96 (t, 6H, NCH$_2$CH$_3$), 1.75 (d, 3H, OCHCH$_3$), 3.06 (q, 4H, NCH$_2$CH$_3$), 3.95 (s, 3H, OCH$_3$), 3.96 (s, 3H, OCH$_3$), 6.15 (q, 1H, OCH(CH$_3$)Ar), 7.11 (s, 1H, ArH), 7.63 (s, 1H, ArH).

EXAMPLE 4

Preparation of 1-[(4',5'-bis(ethoxycarbonylmethoxy)-2'-nitrophenyl)methoxy]-2-oxo-3,3-diethyl- 1-triazene To 3,4-dihydroxybenzaldehyde (5.5 g, 40 mmol) in 50 ml of dry DMF were added 10 g of dried potassium carbonate and ethyl bromoacetate (14.25 g, 85 mmol). The dark solution was stirred under an argon atmosphere for 16 h at 80° C. The reaction mixture was decanted into 200 ml of water. The remaining solid was washed with 50 ml toluene, which was used to extract the product from the water mixture in addition to (3×50 ml) fresh toluene. The solvent was dried with sodium sulfate, filtered and evaporated to give 6.5 g of a brown oil. The product was purified by Kugelrohr distillation (120–130 ° C., 0.01 mm Hg) to give 4.8 g (38% yield) of a colorless oil 4 which solidified on cooling. $^1$NMR: δ 1.30 (t, 6H, OCH$_2$CH$_3$), 4.28 (q, 4H, OCH$_2$CH$_3$), 4.77 (s, 2H, CH$_2$OAr), 4.81 (s, 2H, CH$_2$OAr), 6.94 (d, 1H, ArH), 7.38 (d, 1H, ArH), 7.48 (dd, 1H, ArH), 9.85 (s, 1H, CHO).

Compound 4 (3.25 g, 105 mmol) was added in portions over a period of 30 min to 25 ml of 90% nitric acid cooled to ca. 5 ° C. The solution was stirred an additional 30 min, then poured onto 200 ml of ice. The yellow precipitate that formed was filtered and purified by recrystallization from 95% ethanol to give 2.55 g of a yellow solid. N1VIR showed this material to contain 20% of the dinitration product, 2.5 g (70%) yield) of the desired pale yellow product 5 was obtained by fractional crystallization. $^1$NMR: δ 1.32 (2t, 6H, OCH$_2$CH$_3$), 4.28 (2q, 4H, OCH$_2$CH$_3$), 4.85 (s, 2H, CH$_2$OAr), 4.86 (s, 2H, CH$_2$OAr),7.34 (s,1H, ArH), 7.57 (s, 1H, ArH), 10.42 (s, 1H, CHO).

To a suspension of product 5 (1.5 g, 4.2 mmol) in 30 ml of anhydrous ethanol was added sodium borohydride (50 mg, 1.3 mmol). The reaction mixture was stirred at room temperature for 1 h, during which time the solution became homogeneous. The reaction volume was concentrated by evaporation, 5 ml of water was added and upon cooling a precipitate formed. The pale yellow solid was filtered and recrystallized from 95% ethanol to give 1.1 g (73% yield) of the product 6 as a pale yellow fluffy powder. $^1$NMR: δ 1.31 (2t, 6H, OCH$_2$CH$_3$), 2.5 (br s, 1H, OH), 4.28 (2q, 4H, OCH$_2$CH$_3$), 4.77 (s, 2H, CH$_2$OAr), 4.83 (s, 2H, CH$_2$OAr), 4.95 (s, 2H, HOCH$_2$Ar), 7.18 (s, 1H, ArH), 7.71 (s, 1H, ArH).

To a suspension of the product 6 (400 mg, 1.1 mmol) in 25 ml dry toluene at 5° C. containing 200 μl pyridine, phosphorus tribromide (225 mg, 2.85 mmol) in 2 ml toluene was added dropwise over a period of ca. 30 min under argon. After the addition of PBr$_3$ the reaction was allowed to stir at room temperature. After 20 h, the reaction mixture was filtered, the flitrate was washed with water (3×25 ml), dried with sodium sulfate, filtered and evaporated to give an off-white solid. The solid was triturated with 95% ethanol and upon filtering gave 290 mg (69% yield) of compound 7. $^1$NMR: δ1.30 (2t, 6H, OCH$_2$CH$_3$), 4.28 (2q, 4H, OCH$_2$CH$_3$), 4.77 (s, 2H, CH$_2$OAr), 4.80 (s, 2H, CH$_2$OAr), 4.82 (s, 2H, BrCH$_2$Ar) 6.94 (s, 1H, ArH), 7.64 (s, 1H, ArH).

To a solution of Et$_2$N(N$_2$O$_2$)Na (75 mg, 0.48 mmol) prepared as in Example 1 in 1 ml of dry DMF was added compound 7 (170 mg, 0.4 mmol). The reaction mixture was stirred at room temperature under an argon atmosphere. After 1 h, 20 ml of toluene was added and the mixture was washed with water (3×20 ml) the solvent was dried with sodium sulfate, filtered and evaporated to give the crude product as a yellow oil. The product was purified by chromatography on silica gel eluting with ethyl acetate/hexane (1:3) to give 72 mg (38% yield) of a white solid. $^1$NMR: δ1.08 (t, 6H, NCH$_2$CH$_3$), 1.31 (2t, 6H, OCH$_2$CH$_3$), 3.16 (q, 4H, NCH$_2$CH$_3$), 4.28 (2q, 4H, OCH$_2$CH$_3$), 4.77 (s, CH$_2$OAr), 4.78 (s, 2H, CH$_2$OAr), 5.68 (s, 2H, NOCH$_2$Ar), 7.07 (s, 1H, ArH), 7.73 (s, 1H, ArH).

EXAMPLE 5

Preparation of 1-[(4', 5'-bis(carboxymethoxy)-2'-nitrophenyl)methoxy]-2-oxo-3,3-diethyl-1-triazene potassium salt The compound 8 of Example 4 (27 mg, 55 μmol) was dissolved in 300 μl of dioxane, 500 μl of methanol was added then 60 μl of 1M potassium hydroxide, and an additional 60 μl was added after 1 h at room temperature. After an additional 2 h, the reaction was diluted with 800 μl dioxane. The precipitated product was pelleted by centrifugation, the solvent was removed, the pellet resuspended in ether and pelleted again. The ether was removed and the product was dried under vacuum to give 25 mg (93% yield) of compound 9 as the potassium salt. $^1$NMR (D20O): δ1.06 (t, 6H, NCH$_2$CH$_3$), 3.22 (q, 4H, NCH$_2$CH$_3$), 4.76 (s, 2H, CH$_2$OAr), 4.79 (s, 2H, CH$_2$OAr), 5.85 (s, 2H, NOCH$_2$Ar), 7.14 (s, 1H, ArH), 7.83 (s, 1H, ArH).

EXAMPLE 6

Preparation of 1-[(4',5'-bis(carboxymethoxy)-2'-nitrophenyl)methoxy]-2-oxo-3,3-diethyl-1-triazene acetoxymethyl ester The compound 9 of Example 5 (5 mg, 10 μmol) in 15 0μl water was cooled to 5° C., 25 μl of 1 M HCl was added, a precipitate formed, another 150 μl of water added and the precipitate pelleted by centrifugation. The pellet was washed with cold water and pelleted again, the water removed and the product dried under vacuum to give (3mg, 7.3 μmol) of the free acid. This material was suspended in 200 μl dry methylene chloride; upon addition of 30 μl of diisopropylethylamine, the solution became homogeneous. Bromomethyl acetate (20 μl, 31 mg, 200 μmol) was added and the solution was left at room temperature under argon. After 16 h, the methylene chloride was evaporated and the residue was partitioned between toluene and water. The toluene was dried with sodium sulfate, filtered and evaporated to give an oil. The product was purified by chromatography on silica gel eluting with ethyl acetate/hexane (2:1) to give 2.6 mg (66% yield) of compound 10as an oil. $^1$NMR: δ1.08 (t, 6H, NCH$_2$CH$_3$), 2.14 (2s, 6H, O$_2$CCH$_3$), 3.18 (q, 4H, NCH$_2$CH$_3$), 4.83 (s, 2H, CH$_2$OAr), 4.84 (s, 2H, CH$_2$OAr), 5.67 (s, 2H, NOCH$_2$Ar), 5.85 (s, 4H, CO$_2$CH$_2$O$_2$C), 7.10 (s, 1H, ArH), 7.74 (s, 1H, ArH).

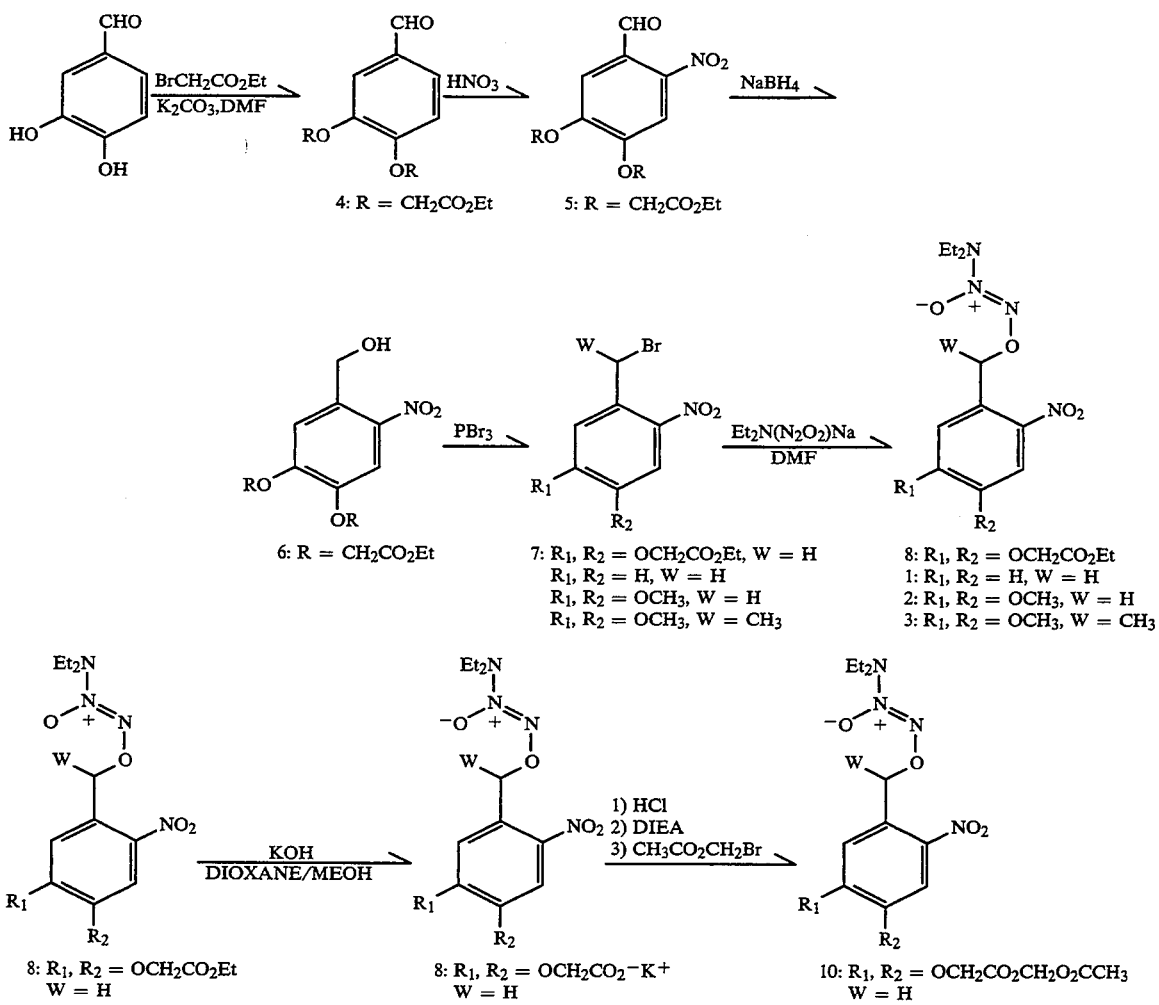

EXAMPLE 7

Determination of Nitric Oxide Release

Nitric oxide release upon photolysis of the compounds of the invention was determined by irradiation of the NO-donors in the presence of deoxyhemoglobin (Hb) either with 365 nm monochromatic light or with light from a Xenon flash lamp for kinetic experiments. FIG. 1 shows the conversion of a 7 μM (heme basis) solution of Hb in 50 mM phosphate degassed with argon which contains 20 μM 1- [(4′, 5′-dimethoxy-2′-nitrophenyl)methoxy]-2-oxo-3,3-diethyl-1-triazene (compound 2). The characteristic absorbance maximum of the Hb at 430 nm is seen to shift to 418 nm upon irradiation with a weak monochromatic light of 365 nm. The shift to 418 nm and the absorbance change in the 500 to 600 nm region are consistent with the formation of nitrosyl hemoglobin Hb(NO). This change was seen for all photo-releasable compounds investigated. Experiments of this type where the absorbance changes as a function of time using a 365 nm light source of known intensity (determined by actinometry) were performed on compounds 2 and 9 (data not shown). From these types of experiments and others using oxyhemoglobin, as well as the determination of nitrite concentrations produced upon irradiation of the NO-donors, the ability of these compounds to produce nitric oxide is without question. Although the yield of nitric oxide molecules per number of photons absorbed by the nitrobenzyl chromophore (quantum yield of nitric oxide production) is quite low at ca. 2% (much the same as that reported for Ru(NO)Cl₃ [Carter T. D. et al., J. Physiol. Abstract C20,, p. 34P (Leeds Meeting 1993)]), physiological concentrations of nitric oxide can easily be obtained with a single powerful light flash typically used in "caged" biological molecule experiments.

Figure 2:
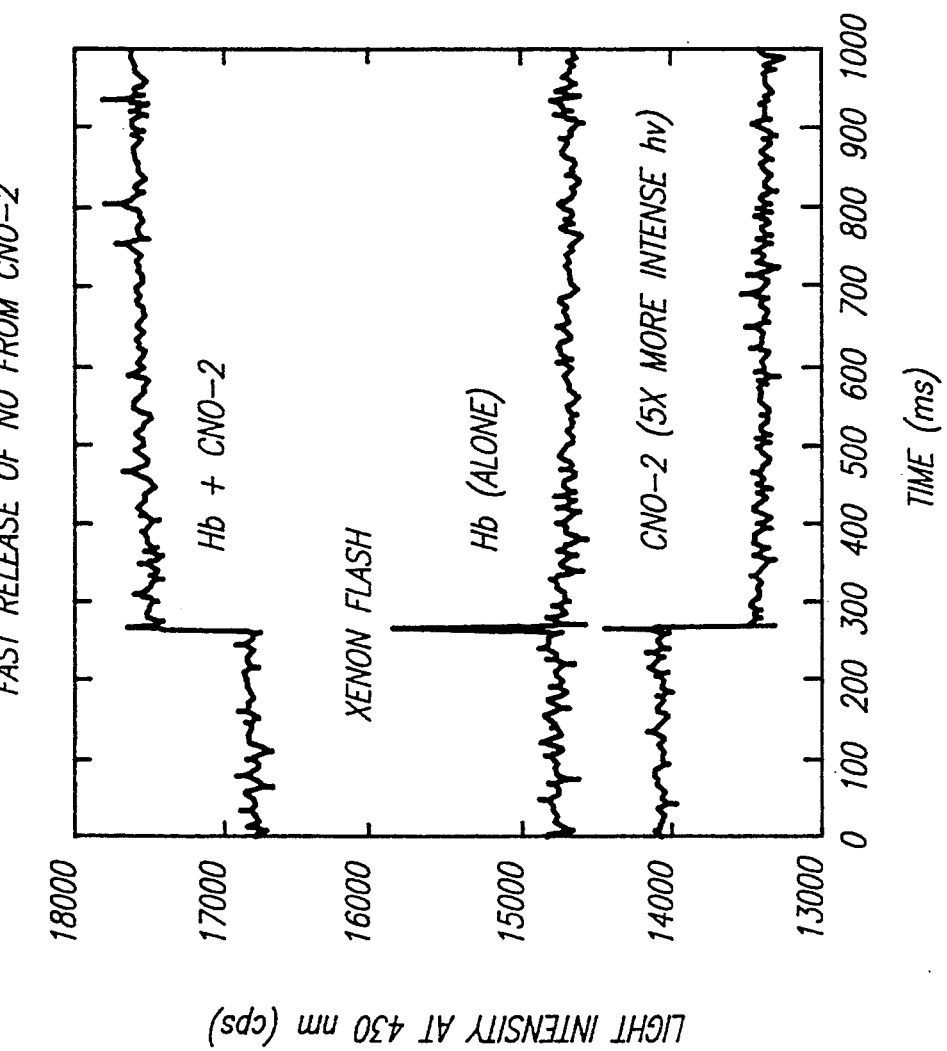
FIG. 2 shows the change in light intensity at 430 nm (with data points taken every 5 milliseconds) in three experiments to analyze the release of NO.
Figure 3:
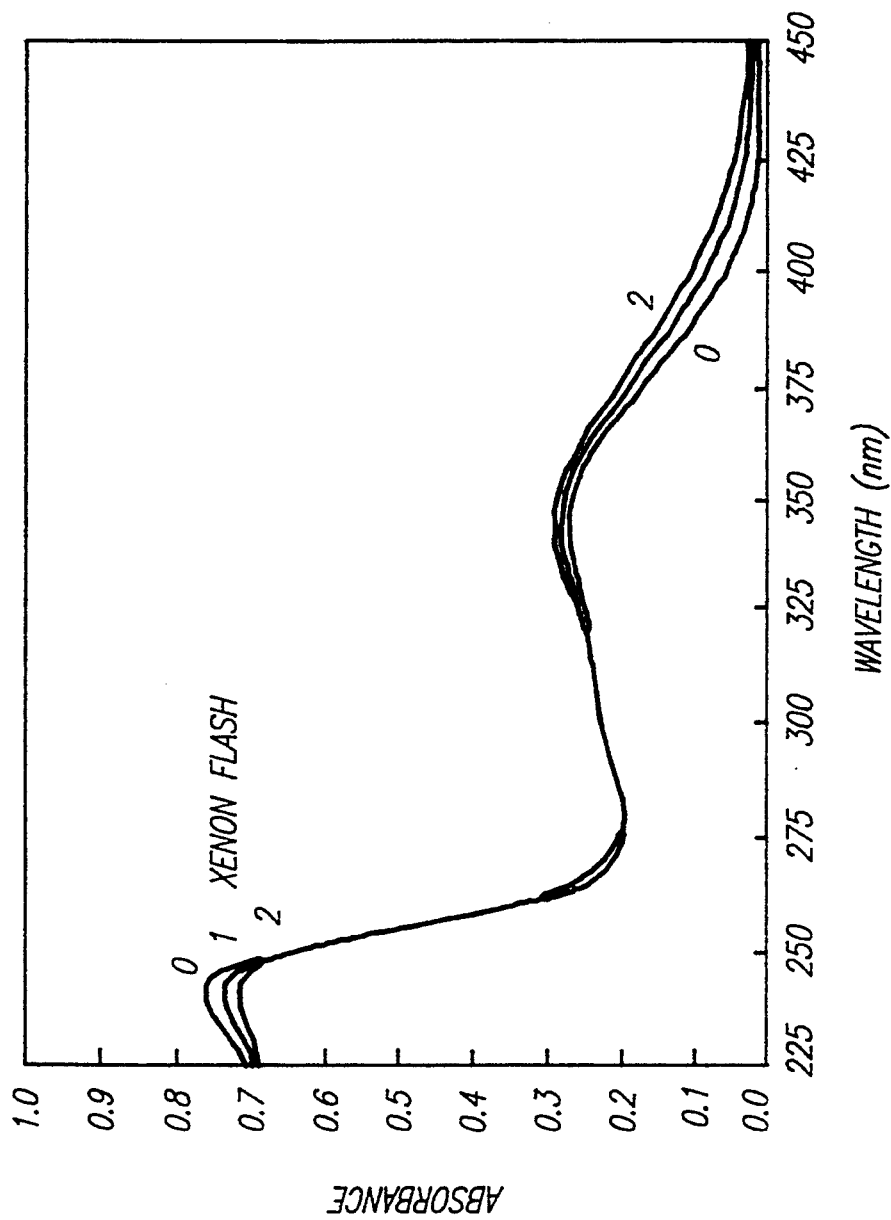
FIG. 3 shows the changes in the absorbance spectrum over the wavelengths from 225 to 450 nm upon Xenon lamp photolysis of a compound in accordance with the present invention.

Irradiation of a degassed solution of Hb in the presence of compound 2 with a single pulse from a filtered (>340 nm) Xenon lamp results in the release of nitric oxide in less than 5 milliseconds, which is as fast as the available instrumentation could detect. FIG. 2 shows the change in light intensity at 430 nm (with data points taken every 5 milliseconds) in three experiments; in this figure, an increase in light intensity corresponds to a decrease in absorbance. The top trace shows the decrease in the absorbance at 430 nm as Hb is converted to Hb(NO); this occurs in about 5 milliseconds (one data point) after the excitation of a 100 μM solution of compound 2. The middle trace shows the same experiment with Hb in the absence of the nitric oxide donor 2; as expected, no change in the absorbance of the Hb is observed, apart from a flash artifact. The bottom trace shows the increase in absorbance at this wavelength from a solution of compound 2 alone, which results from a flash about five times more intense than that used in the experiments with Hb. FIG. 3 shows the change in the absorbance spectrum from 225 to 450 nm upon Xenon lamp photolysis of compound 2. This experiment shows that the absorbance from the photoproducts of compound 2 is not responsible for the change observed in the presence of Hb and occurs with a similar rate constant or faster than that seen for the loss of Hb as it is converted to Hb(NO). Irradiation of an equal concentration of Hb with compound 6 (which should produce the same photoproducts except for nitric oxide) shows only an increase in absorbance (data not shown) similar to that seen in the lower trace in FIG. 2.

The observed fast release of nitric oxide from the compounds of the present invention has many advantages, as many biological events (particularly, for example, in nerve cells) occur on similar time scales. In many experiments, a slow release of nitric oxide (as is the case which most other known NO-donors) simply would not be acceptable. Even when very rapid release of nitric oxide is not necessary, it is frequently desired to generate nitric oxide specifically inside the tissue or at some distance from the injection or delivery site. Previous nitric oxide donors begin releasing NO and decomposing immediately and therefore will exert their major effects at the injection or delivery site. In contrast, the novel compounds of the invention are biologically inert before illumination and can be allowed to diffuse to or become trapped at a desired remote site of action, after which illumination releases the NO specifically at the desired location. Accordingly, the novel compounds of the invention enable researchers to carry out a wide variety of experiments with a degree of control over the timing and location of NO release which was not heretofore possible.

EXAMPLE 8

Biological Testing

Human platelets were prepared in a manner similar to that described by Hallam, T.J. and T.J. Rink, FEBS Lett. 186:175 (1985). The platelets were obtained from the blood of healthy human donors who had not ingested aspirin for at least two weeks. After removal from the vein, the blood was quickly added to a centrifuge tube containing 0.15 volumes of acid citrate dextrose (70 mM citric acid, 85 mM trisodium citrate, 110 mM dextrose). The anticoagulated blood was centrifuged at 500 x g for 20 minutes to pellet the platelets. The platelet-poor plasma (PPP) was carefully removed and the pellet resuspended with resuspension buffer in a volume equal to the PPP removed. The resuspension buffer contained 138 mM NaCl, 2.7 mM KCl, 1.1 mM $KH_2PO_4$, 8.1 mM $Na_2HPO_4$, 0.5 mM $MgCl_2$, 10 mM glucose, 10 mM Hepes adjusted to pH=7.4. The platelets were kept at 5°-10° C. in plastic centrifuge tubes with continuous gentle swirling until used in the aggregation experiments within a maximum of 6 hours.

Aggregation of platelets in 0.5 ml volumes was monitored by continuous recording of light transmission in a Chronolog Dual Channel Aggregometer (Chrono-Log, Haverston, Pa.). The platelets were incubated at 37° C. with stirring (1100 rpm) for 3 minutes prior to the addition of the compounds of the invention. In a typical experiment, 40 μM of 1-[(4', 5'-dimethoxy-2'nitrophenyl) methoxy]2-oxo-3,3-diethyl-l-triazene (compound 2) was added to the suspension of platelets and the solution was irradiated with a weak 365 nm light for 4 minutes; this only partially photolysed the sample. At this point, 40 milliunits/ml of thrombin was added to induce aggregation.

FIG. 4 shows a typical aggregation experiment as described above. The first trace shows complete aggregation induced by thrombin in the absence of the nitric oxide donor. In the second trace, compound 2 was added and irradiated in the manner described. Upon addition of thrombin, almost complete inhibition of aggregation was observed. Similar results were obtained with 1-[(3', 4'-bis (carboxymethoxy)-2'-nitrophenyl)methoxyl]-2oxo- 3,3- diethyl-1triazene potassium salt (compound 9); however, the inhibition of platelet aggregation can be completely abolished by the addition of extracellular hemoglobin (a nitric oxide sponge) with this nitric oxide donor. This demonstrates that compound 9 is not able to cross the cell membrane. With the ester derivative 1-[(4',5'- bis (carboxylmethyloxy)-2'-nitrophenyl)methyloxo]-2- oxo-3,3-diethyl-1-triazene acetoxymethyl ester (compound 10), which is cell-permeable and able to concentrate in the cell, complete inhibition of aggregation occurred at a concentration of just 20 μM in both the presence and the absence of hemoglobin with incubation times of only 10 minutes.

From the foregoing description, one skilled in the art can readily ascertain the essential characteristics of the invention and, without departing from the spirit and scope thereof, can adapt the invention to various usages and conditions. Changes in form and substitution of equivalents are contemplated as circumstances may suggest or render expedient, and any specific terms employed herein are intended in a descriptive sense and not for purposes of limitation.

We claim:

1. A compound of the formula $$A-N^+(O^-)=N-O-B \qquad (I)$$

wherein A is selected from the group consisting of $-NR^1R^2$ 1-imidazolyl and $-OR^3$, in which $R^1$ selected from the group consisting of hydrogen and $C_1$–$C_{12}$ alkyl, $R^2$ is selected from the group consisting of hydrogen, $C_1$–$C_{12}$ alkyl, $-(CR''_2)$ $yNR'_2$, $-CR''_2CO_2R^2$, $-CR''_2CO_2CR''_2O_2CR''$ and $-C(CO_2R'')$ $R''R^4$, $R^3$ is selected from the group consisting of hydrogen, $C_1$–$C_{12}$ alkyl, $-C_6H_5$ and B, each R' is independently selected from the group consisting of hydrogen, lower alkyl, $-(CR''_2)$ $yNR''_2$, $-CR''_2CO_2R''$ and $-CR''_2CO_2CR''_2O_2CR''$, $R''$ is hydrogen or lower alkyl, each y is an integer from 1 to 6 and $R^4$ is an amino acid side-chain residue characteristic of a naturally-occurring amino acid and is selected from the group consisting of alkyl, hydroxyalkyl and aralkyl; and B is a group labile to photolysis selected from the group consisting of α-benzoyl-3, 5- dimethoxybenzyl, 3,5-dinitrophenyl, (4- methoxy-8azido-1-naphthyl) methyl and groups of the formula

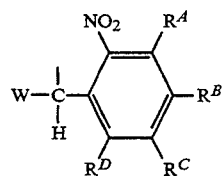

wherein $R^A$ is selected from the group consisting of hydrogen, lower alkyl, lower alkoxy, $-(CR''_2)_y$ SR', $-(CR''_2)_yNR''_2$, $-CO_2R$ and $-OCR''$-

$_2CO_2R$, in which R is selected from the group consisting of hydrogen, $C_1$-$C_{12}$ alkyl, —(CR''$_2$)$_y$O$_2$CR' and R', R'' and y are as previously defined;

each of $R^B$ and $R^C$ is independently selected from the group consisting of hydrogen, lower alkyl, lower alkoxy, —CO$_2$R and —OCR''$_2$CO$_2$R, or $R^B$ and $R^C$ taken together are —O(CR''$_2$)$_x$O—, in which x is 1 or 2;

$R^D$ is selected from the group consisting of NO$_2$, hydrogen, lower alkyl, lower alkoxy, —(CR''$_2$)$_y$SR', —CO$_2$R, —COR and —OCR''$_2$CO$_2$R; and W is selected from the group consisting of hydrogen, lower alkyl, CO$_2$R'' and

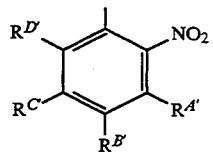

wherein each of $R^{A'}$, $R^{B'}$, $R^{C'}$ and $R^{D'}$ is independently defined in the same manner as $R^A$, $R^B$, $R^C$ and $R^D$, respectively.

2. A compound according to claim 1, wherein B is selected from the group consisting of 2-nitrobenzyl, 2(2-nitrophenyl)ethyl and α-carboxy-2-nitrobenzyl, 2,2'-dinitrobenzhydryl, 4,5-dimethyoxy- 2nitrobenzyl, 1(4,5-dimethoxynitrophenyl) ethyl, bis (2-nitro-4,5-dimethoxyphenyl)methyl, α-benzoyl-3,5-dimethoxybenzyl, 3,5-dinitrophenyl, and (4-methyoxy-8 azido-1-naphthyl)methyl.

3. A compound according to claim 1, wherein B has the formula

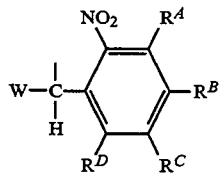

wherein $R^A$ is selected from the group consisting of hydrogen, lower alkyl, lower alkoxy, —(CR'$_2$)$_y$SR', —(CR''$_2$)$_y$-NR''$_2$—CO$_2$R and —OCR''$_2$CO$_2$R, in which R is selected from the group consisting of hydrogen, $C_1$-$C_{12}$ alkyl, —(CR''$_2$)$_y$O$_2$CR' and R', R'' and y are as previously defined;

each of $R^B$ and $R^C$ is independently selected from the group consisting of hydrogen, lower alkyl, lower alkoxy, —CO$_2$R and —OCR''$_2$CO$_2$R, or $R^B$ and $R^C$ taken together are —O(CR''$_2$)$_x$O—, in which x is 1 or 2;

$R^D$ is selected from the group consisting of NO$_2$, hydrogen, lower alkyl, lower alkoxy, —(CR''$_2$)$_y$SR', —CO$_2$R, —COR and —OCR''$_2$CO$_2$R; and W is selected from the group consisting of hydrogen, lower alkyl, CO$_2$R'' and

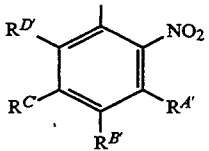

wherein each of $R^{A'}$, $R^{B'}$, $R^{C'}$ and $R^{D'}$ is independently defined in the same manner as $R^A$, $R^B$, $R^C$ and $R^D$, respectively.

4. A compound according to claim 3, wherein $R^A$ and $R^D$ are hydrogen, $R^B$ and $R^C$ are hydrogen or lower alkoxy and W is hydrogen, lower alkyl or

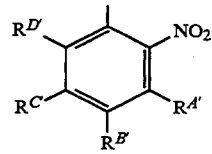

wherein each of $R^{A'}$, $R^{B'}$, $R^{C'}$ and $R^{D'}$ is independently defined in the same manner as $R^A$, $R^B$, and $R^C$ and $R^D$, respectively.

5. A compound according to claim 3, wherein $R^A$ and $R^D$ are hydrogen, $R^b$ and $R^C$ are —CO$_2$R or —OCR''$_2$CO$_2$R, in which R is selected from the group consisting of hydrogen and —(CR''$_2$)$_y$O$_2$CR'' in which R'' is hydrogen or lower alkyl, and W is hydrogen, lower alkyl or

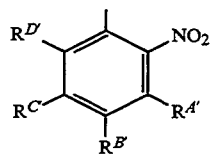

wherein each of $R^{A'}$, $R^{B'}$, $R^{C'}$ and $R^{D'}$ is independently defined in the same manner as $R^A$, $R^B$, $R^C$ and $R^D$, respectively.

* * * * *

UNITED STATES PATENT AND TRADEMARK OFFICE
CERTIFICATE OF CORRECTION

PATENT NO. : 5,374,710  Page 1 of 3

DATED : December 20, 1994

INVENTOR(S) : Roger Y. Tsien and Lewis R. Makings

It is certified that error appears in the above-indentified patent and that said Letters Patent is hereby corrected as shown below:

| Column | Line | |
|---|---|---|
| Abstract | 7 | Cancel "lablie" insert --labile-- |
| 1 | 49 | Cancel "antino" insert --amino-- |
| 2 | 15 | Cancel "enzyrnatic" insert --enzymatic-- |
| 2 | 58 | Cancel "et at." and insert --et al.-- |
| 5 | 6 | Cancel "aminoallcyl" and insert --aminoalkyl-- |
| 5 | 32 | Delete "," first occurrence |
| 7 | 15 | Cancel "diethyl 1triazene" and insert --diethyl-1-triazene-- |
| 8 | 23 | Cancel "CH$_3$" first occurrence and insert --C$\underline{H}_3$-- |
| 8 | 23 | Cancel "NCH$_2$" second occurrence and insert --NC$\underline{H}_2$-- |
| 8 | 29 | Cancel "4'" and insert --5'-- |
| 8 | 46 | Cancel "CH$_3$" and insert --C$\underline{H}_3$-- |
| 8 | 47 | Cancel "NCH$_2$" and insert --NC$\underline{H}_2$-- |
| 8 | 53 | Cancel "4'" and insert --5'-- |
| 8 | 54 | Cancel "diethyl 1triazene" and insert --diethyl-1-triazene-- |
| 9 | 3 | Cancel "CH$_3$" first occurrence and insert --C$\underline{H}_3$-- |
| 9 | 3 | Cancel "NCH$_2$" and insert --NC$\underline{H}_2$-- |
| 9 | 25 | Cancel "CH$_3$" and insert --C$\underline{H}_3$-- |
| 9 | 26 | Cancel "OCH$_2$" and insert --OC$\underline{H}_2$-- |

UNITED STATES PATENT AND TRADEMARK OFFICE
CERTIFICATE OF CORRECTION

PATENT NO. : 5,374,710

DATED : December 20, 1994

INVENTOR(S) : Roger Y. Tsien and Lewis R. Makings

It is certified that error appears in the above-indentified patent and that said Letters Patent is hereby corrected as shown below:

| Column | Line | |
|---|---|---|
| 9 | 35 | Cancel "N1VIR" and insert --NMR-- |
| 9 | 39 | Cancel "CH3" first occurrence and insert --C$\underline{H}_3$-- |
| 10 | 16 | Cancel "NCH2" and insert --NC$\underline{H}_2$-- |
| 10 | 16 | Cancel "OCH2" and insert --OC$\underline{H}_2$-- |
| 10 | 35 | Cancel "(D20O)" and insert --(D$_2$O)-- |
| 10 | 36 | Cancel "CH3" first occurrence and insert --C$\underline{H}_3$-- |
| 10 | 36 | Cancel "NCH2" second occurrence and insert --NC$\underline{H}_2$-- |
| 10 | 64 | Cancel "CH3" and insert --C$\underline{H}_3$-- |
| 10 | 65 | Cancel "NCH2" and insert --NC$\underline{H}_2$-- |
| 14 | 10 | Cancel "3', 4'" and insert --4', 5'-- |
| 14 | 11 | Cancel "diethyl-1triazene" and insert --diethyl-1-triazene-- |

UNITED STATES PATENT AND TRADEMARK OFFICE
CERTIFICATE OF CORRECTION

PATENT NO. : 5,374,710

DATED : December 20, 1994

INVENTOR(S) : Roger Y. Tsien and Lewis R. Makings

It is certified that error appears in the above-indentified patent and that said Letters Patent is hereby corrected as shown below:

| Column | Line | |
|---|---|---|
| 14 | 55 | Cancel "8azido" and insert --8-azido-- |
| 15 | 29 | Cancel "2nitrobenzyl" and insert --2-nitrobenzyl-- |
| 15 | 32 | Cancel "8azido" and insert --8-azido-- |
| 15 | 46 | Cancel "(CR'$_2$)" and insert --(CR"$_2$)-- |

Signed and Sealed this

Third Day of October, 1995

Attest:

BRUCE LEHMAN

Attesting Officer     Commissioner of Patents and Trademarks